(12) United States Patent
Finarov et al.

(10) Patent No.: US 7,477,405 B2
(45) Date of Patent: Jan. 13, 2009

(54) METHOD AND SYSTEM FOR MEASURING PATTERNED STRUCTURES

(75) Inventors: Moshe Finarov, Rehovot (IL); Boaz Brill, Rehovot (IL)

(73) Assignee: Nova Measuring Instruments Ltd., Rehovot (IL)

( * ) Notice: Subject to any disclaimer, the term of this patent is extended or adjusted under 35 U.S.C. 154(b) by 472 days.

(21) Appl. No.: 10/724,113

(22) Filed: Dec. 1, 2003

(65) Prior Publication Data
US 2004/0109173 A1    Jun. 10, 2004

Related U.S. Application Data

(63) Continuation of application No. 09/610,889, filed on Jul. 6, 2000, now Pat. No. 6,657,736.

(30) Foreign Application Priority Data
Jul. 9, 1999    (IL)    ............................. 130874

(51) Int. Cl.
*G01B 11/14* (2006.01)

(52) U.S. Cl. ..................................... 356/625

(58) Field of Classification Search ................ 356/625, 356/630, 237.2
See application file for complete search history.

(56) References Cited

U.S. PATENT DOCUMENTS

| | | | |
|---|---|---|---|
| 4,330,213 A | 5/1982 | Kleinknecht et al. | |
| 4,710,642 A | 12/1987 | McNeil | |
| 4,905,170 A | 2/1990 | Forouhi et al. | |
| 4,999,014 A | 3/1991 | Gold et al. | |
| 5,007,708 A | 4/1991 | Gaylord et al. | |
| 5,164,790 A | 11/1992 | McNeil et al. | |
| 5,361,137 A | 11/1994 | Aton et al. | |
| 5,555,474 A * | 9/1996 | Ledger | ........................ 356/632 |
| 5,607,800 A | 3/1997 | Ziger | |
| 5,682,242 A | 10/1997 | Eylon | |
| 5,703,692 A | 12/1997 | McNeil et al. | |
| 5,798,837 A * | 8/1998 | Aspnes et al. | ................ 356/369 |

(Continued)

OTHER PUBLICATIONS

N. Chateau et al, "Algorithm for the rigorous coupled-wave analysis of grating diffraction", *Journal of the Optical Society of America* A, vol. 11, No. 4, Apr. 1994, pp. 1321-1331.

(Continued)

*Primary Examiner*—Roy M Punnoose
(74) *Attorney, Agent, or Firm*—Browdy and Neimark, P.L.L.C.

(57) ABSTRACT

A measurement method and system configured to determine parameters of a structure during production, the system including: a stage configured to support the structure during measurements; a measuring unit coupled to the stage; and a processor coupled to the measuring unit. The measuring unit includes: an illumination system configured to direct incident light of substantially broad wavelengths band toward a surface of the structure during measurements; and a detection system coupled to the illumination system and configured to detect light propagating from the surface of the structure during measurements. The measuring unit is configured to generate one or more output signals in response to the detected light during measurements. The processor is configured to determine the parameters of the structure from the one or more output signals during measurements. The parameters include a critical dimension of the structure and a layer characteristic of the structure.

96 Claims, 8 Drawing Sheets

U.S. PATENT DOCUMENTS

| | | | |
|---|---|---|---|
| 5,867,276 | A | 2/1999 | McNeil et al. |
| 5,867,590 | A | 2/1999 | Eylon |
| 5,889,593 | A | 3/1999 | Bareket |
| 5,963,329 | A | 10/1999 | Conrad et al. |
| 5,978,074 | A * | 11/1999 | Opsal et al. .................... 356/72 |
| 6,045,433 | A | 4/2000 | Dvir et al. |
| 6,076,465 | A * | 6/2000 | Vacca et al. ................. 101/481 |
| 6,278,519 | B1 * | 8/2001 | Rosencwaig et al. ........ 356/369 |
| 6,297,880 | B1 * | 10/2001 | Rosencwaig et al. ........ 356/369 |
| 6,363,166 | B1 * | 3/2002 | Wihl et al. .................. 382/144 |
| 6,426,502 | B1 * | 7/2002 | Finarov ....................... 250/348 |
| 6,483,580 | B1 * | 11/2002 | Xu et al. ..................... 356/300 |
| 6,633,831 | B2 * | 10/2003 | Nikoonahad et al. ........ 702/155 |

OTHER PUBLICATIONS

T. Gaylord et al, "Analysis and Applications of Optical Diffraction by Gratings", *Proceedings of the IEEE*, vol. 73, No. 5, May 1985, pp. 894-938.

E. Glytsis et al, "Review of rigorous coupled-wave analysis and of homogeneous effective medium approximations for high spatial-frequency surface-relief gratings", *Conference on Binary: Optics*, Feb. 23-25, 1993, pp. 62-76.

E. Glytsis et al, "Rigorous coupled-wave analysis and applications of rating diffraction", *Diffractive and Miniaturized Optics, Critical Reviews of Optical Science and Technology*, vol. CR49, Jul. 12-13, 1993, pp. 3-31.

R. Krukar et al, "Overlay and grating line shape metrology using optical scatterometry: final report", Aug. 31, 1993, *DARPA, U.S. Army Missile Command*, p. 28.

R. Krukar et al, "Reactive ion etching profile and depth characterization using standard and neutral network analysis of light scattering data", *J. Appl. Phys.* vol. 74, No. 6, Sep. 15, 1993.

S. Lee et al, "More stable algorithm for rigorous coupled wave analysis applied to topography simulation in optical lithography and its numerical implementation", *Optical Microlithography IX, SPIE*, vol. 2726, Mar. 13-15, 1996, pp. 288-298.

J.M. Leng et al, "Simultaneous measurement of six layers in a silicon on insulator film stack using spectrophotometry and beam profile reflectometry", *Journal of Applied Physics*, vol. 81, No. 8, Apr. 1997, pp. 3570-3578.

D. Mills et al, "Spectral ellipsometry on patterned wafers", *Process, Equipment, and Materials Control in Integrated Circuit Manufacturing, SPIE* vol. 2637, Oct. 25-26, 1995, pp. 194-203.

S. Peng et al, "Efficient implementation of rigorous coupled-wave analysis for surface-relief gratings", *J. Opt. Soc. Am. A*, vol. 12, No. 5, May 1995, pp. 1087-1096.

D. Ziger et al, "Linesize effects on ultraviolet reflectance spectra", *Optical Engineering*, Jan. 1997, vol. 36, No. 1, pp. 243-250.

Z. Zylberberg et al, "Rogorous coupled-wave analysis of pure reflection gratings", *J. Opt. Soc. Am.*, vol. 73, No. 3, Mar. 1983, pp. 392-398.

\* cited by examiner

METHOD AND SYSTEM FOR MEASURING PATTERNED STRUCTURES

CROSS REFERENCE TO RELATED APPLICATION

This application is a continuation of application Ser. No. 09/610,889, filed Jul. 6, 2000, now U.S. Pat. No. 6,657,736.

FIELD OF THE INVENTION

This invention is in the field of measurement techniques, and relates to an optical system and method for the accurate measurement of parameters of regular patterned structures. The invention is particularly useful in controlling a lithography process.

BACKGROUND OF THE INVENTION

Lithography is widely used in various industrial applications, including the manufacture of integrated circuits, flat panel displays, micro-electro-mechanical systems, micro-optical systems etc. Generally speaking, the lithography process is used for producing a patterned structure. During the manufacture of integrated circuits, a semiconductor wafer undergoes a sequence of lithography-etching steps to produce a plurality of spaced-apart stacks, each formed by a plurality of different layers having different optical properties. Each lithography procedure applied to the wafer results in the pattern on the uppermost layer formed by a plurality of spaced-apart photoresist regions.

To assure the performance of the manufactured products, the applications of the kind specified above require accurate control of the dimensions of the sub-micron features of the obtained pattern. When dealing with wafers, the most frequently used dimensions are the layer thickness and the so-called "critical dimension" (CD). CD is the smallest transverse dimension of the developed photoresist, usually the width of the finest lines and spaces between these lines. Since the topography of the measured features is rarely an ideal square, additional information found in the height profile, such as slopes, curves etc., may also be valuable in order to improve the control of the fabrication process.

Generally, an ordinary optical microscope can be used for measuring features' dimensions. A microscope is practically capable of measuring line width with a resolution of no less than 0.1 μm. The current high-performance semiconductor devices, however, have features' dimensions of 0.18 μm, and require CD measurement with the resolution of a few nanometers.

Several Optical CD (OCD) measurement techniques recently developed rely on imaging a certain test pattern which is placed in a special test area of the wafer. These techniques utilize various methods aimed at amplifying tiny differences in the line-width to obtain macroscopic effects that could be resolved by visible light, although the original differences are more than two orders of magnitude below the wavelength used. However, some of these techniques do not rely on fundamental physical effects, and thus could be more effective in some cases and less effective in others.

Another kind of technique utilizes scatterometric measurements, i.e., measurements of the characteristics of light scattered by the sample. To this end, a test pattern in the form of a grating is usually placed in the scribe line between the dies. The measurement includes the illumination of the grating with a beam of incident light and determining the diffraction efficiency of the grating under various conditions. The diffraction efficiency is a complicated function of the grating line profile and of the measurement conditions, such as the wavelength, the angle of incidence, the polarization and the diffraction order. Thus, it is possible to gather a wealth of data thereby allowing the extraction of information about the line profile.

Techniques that utilize the principles of scatterometry and are aimed at the characterization of three-dimensional grating structures and the determination of line profiles have been disclosed in numerous publications. Publications, in which diffraction efficiency was measured versus wavelength, include, for example the following:

(1) A. Roger and D. Maystre, J. Opt. Soc. Am, 70 (12), pp. 1483-1495 (1979) and A. Roger and D. Maystre, Optica Acta, 26 (4), pp. 447-460 (1979) describe and systematically analyze the problem of reconstruction of the line profile of a grating from its diffraction properties (the inverse scattering problem). A later article "Grating Profile Reconstruction by an Inverse Scattering Method", A. Roger and M. Breidne, Optics Comm., 35 (3), pp. 299-302 (1980) discloses how the idea disclosed in the above articles can be experimentally used. The experimental results show that the line profile can be fitted such that the calculated diffraction efficiency will closely match the diffraction efficiency measured as a function of wavelength for "−1" diffraction order. The comparison of these experimental results with electron microscopy measurement showed a reasonable agreement.

(2) "Reconstruction of the Profile of Gold Wire Gratings: A comparison of Different Methods", H. Lochbihler et. al., Optik, 98 (1), pp. 21-25 (1994) deals with the comparison of the results of several experimental techniques. Both optical transmittance and reflectance efficiencies were measured in the "0" order as a function of wavelength. By fitting the measurements to theoretical spectra calculated using diffraction theory, the grating profile was found. Comparison of these results with the results of X-ray diffraction efficiency and electron microscopy showed a good agreement.

(3) Voskovtsova, L. M. et al., Soviet Journal of Optical Technology 60 (9) pp. 617-19 (1993) studies the properties of gratings fabricated by replica technique. It has been found that the line profile of the hologram diffraction grating differs from the calculated sinusoidal profile. This difference leads to a difference in the spectral diffraction efficiency, an effect that was utilized for process control.

(4) Savitskii, G. M. and Golubenko, I. V., Optics and Spectroscopy 59 (2), pp. 251-4 (1985) describes a theory for the reflection properties of diffraction gratings with a groove profile which is a trapezoid with rounded corners. Such gratings can be fabricated by a holographic technique with photosensitive materials. It was found that the parameters of the trapezoidal profile, such as the depth of the groove, the width of a flat top and the slope of the side walls, affect the diffraction efficiency of the grating working in the auto collimation regime for the "−1" order.

(5) Spikhal'skii A. A., Opt Commun 57 (6) pp. 375-379 (1986) presents the analysis of the spectral characteristics of gratings etched into a dielectric material. It has been found that these characteristics can be significantly varied by slightly changing the grating groove profile.

(6) U.S. Pat. No. 5,867,276 discloses a technique for broadband scatterometry, consisting of the illumination of a sample with an incident light beam having a broad spectral composition and detecting a beam of light diffracted from the sample with a spectrometer. The technique is aimed at obtaining the spectrally-resolved diffraction characteristics of the sample for determining the parameters of the sample. The patent suffers from the following drawbacks: the measurements are done in the "0" diffraction order which is insensitive to asymmetries in the profile; and the analysis is done using the Neural Network (N.N.) method, which is sub-optimal by nature for applications requiring a high resolution. Additionally, the method does not take into account the need to focus the light onto a small spot, which is determined by the small area of the test structure allowed in the scribe line.

According to another group of publications, a monochromatic light source (e.g. laser) is utilized, and grating profile parameters are extracted from the measurement of the diffraction efficiency versus incidence angle. Such publications include, for example the following:

(A) S. S. H. Naqvi et al., J. Opt. Soc. Am. A, 11 (9), 2485-2493 (1994) discloses a technique that utilizes measurement of the diffraction efficiency in "0" order versus incidence angle to find the height of etched grating. Calculations are based on the Rigorous Coupled Wave Theory (RCWT), initially developed by Moharam and Gaylord and disclosed in M. G Moharam and T. K. Gaylord, J. Opt. Soc. Am, 71, pp. 811-818 (1981), and several existing statistical techniques for the fitting stage.

(B) Raymond, J. R. et al., SPIE 3050, pp. 476-486 (1997) discloses a technique that utilizes a laser beam scanning with a range of angles to measure the diffraction efficiency versus incidence angle and to extract the line profile from the measured data.

(C) U.S. Pat. Nos. 4,710,642 and 5,164,790 disclose optical instruments which require to rotate the sample under test, which is definitely a disadvantage.

(D) U.S. Pat. Nos. 4,999,014; 5,889,593 and 5,703,692 disclose instruments employing angle-dependent intensity measurements without the requirement to rotate the sample. According to these techniques, different optical arrangements are used for providing the changes of the angle of incidence of an illuminating monochromatic beam onto the sample (wafer), without moving the sample. According to U.S. Pat. No. 5,703,692, the measurement is carried out by mechanically scanning the angle of incidence using a rotating block. The main disadvantages of such a technique are as follows: it requires the use of moving parts, the calibration of an angle in a dynamical situation, and has a limited angle range which does not provide enough information allowing accurate extraction of profile. According to U.S. Pat. No. 5,889,593, an optical arrangement includes a first lens that serves for focusing incident light onto a wafer at a range of angles, and a second lens that serves for focusing diffracted light onto a detector array. Although this technique does not need any moving parts, since the measurements are simultaneous, special care has to be taken to destroy coherence and avoid interference between the different light paths. Any suitable component for destroying the coherence always reduces the system resolution, thereby reducing the amount of obtained information.

In a third group of publications, the diffraction efficiency is measured when both wavelength and incidence angle are constant. In this case, information is extracted from the comparison of diffraction efficiency of several orders. This group of publications includes, for example, the following documents:

(I) U.S. Pat. No. 4,330,213 discloses a line-width measurement system using a diffraction grating. In this system, the intensities of first and second order light components are obtained to determine the line-width using empirical formulae.

(II) U.S. Pat. No. 5,361,137 discloses another example of the use of a conventional scatterometry technique. Here, a set of intensities of the "1" or "2" diffraction order image of the set of "fixed-line width and variable-pitch-width" test gratings is recorded. From this set of intensities, line-width can be calculated.

Generally speaking, the conventional techniques use the following methodology in order to analyze the measured results:

First, a model is assumed for the grating profile having a number of parameters that uniquely define the profile. The user defines the required model (type of model) and sets the limits and the required resolution for each of the desired parameters.

Second, a spectral library is prepared using an optical model. The spectral library contains the calculated spectra for all possible profiles as defined by the user.

Third, given a measured spectrum, a fitting procedure finds the profile whose calculated spectrum included in the spectral library best matches the measured spectrum.

SUMMARY OF THE INVENTION

There is accordingly a need in the art to facilitate the control of the manufacture of patterned structures by providing a novel method and system for measurements in a patterned structure to determine a line profile of the structure, utilizing the principles of scatterometry.

The term "patterned structure" signifies a structure comprising a plurality of spaced-apart stacks (elements) each including different layers, the pattern being formed by patterned regions and un-patterned regions. The term "pattern region" used herein signifies is a region including elements (stacks) having different optical properties, and the term "un-patterned region" signifies a region with substantially uniform optical properties, as compared to the patterned region. Such an un-patterned region is comprised of a single stack including different layers having different optical properties.

The main idea of the present invention is based on obtaining measured data from at least two measurements applied to the same patterned structure (e.g., wafer) in order to achieve both high accuracy and high reliability measurements. The entire measurement procedure is carried out is several steps, taking a different measurement at each step. Analysis, likewise, is performed in several steps, wherein each analysis step utilizes the information obtained in the previous steps. The two measurements could be applied at two different measurement sites located, respectively, in patterned and un-patterned regions. The two measurements may be carried out so as to detect light returned from the structure with different solid angles of propagation, or with different states of polarization.

According to the present invention, at least one parameter of the profile considered in an optical model used for measurements is determined by analyzing at least one preliminary measurement applied to a predetermined site on the structure (wafer). The preliminary measurement is inherently different from further measurements by either the type of site under measurements or the measurement conditions (angle, polarization, wavelength range, diffraction order, etc.). For example, the preliminary measurement utilizes normal incidence of an illuminating beam, while the further measurement utilizes oblique illumination. Data (parameters) obtained through this preliminary measurement is used for optimizing the fitting procedure, thereby improving further measurements applied to other locations on the structure.

Preferably, the parameters obtained through the preliminary measurement include the reflectivity and thickness of at least one layer underneath the uppermost layer. Additionally, the at least one preliminary measurement allows for determining optical constants (i.e., refraction and absorption coefficients n and k) and thickness of the regions of the uppermost layer.

There is thus provided according to one aspect of the present invention, a method of determining a line profile in a patterned structure for controlling a process of manufacture thereof, wherein the patterned structure comprises a plurality of different layers, the pattern in the structure being formed by patterned regions and un-patterned regions, the method comprising the steps of:

carrying out at least first and second measurements, each of the measurements utilizing illumination of the structure with a broad wavelengths band of incident light which is directed on the structure at a certain angle of incidence, detection of spectral characteristics of light returned from the structure, and generation of measured data representative thereof;

analyzing the measured data obtained with the first measurement and determining at least one parameter of the structure; and analyzing the measured data obtained with the second measurement and utilizing said at least one parameter for determining the profile of the structure.

According to another aspect of the present invention, there is provided a measurement system for determining a line profile in a patterned structure comprising a plurality of different layers, the pattern in the structure being formed by patterned regions and un-patterned regions, the system comprising a measuring unit including an illumination assembly and a collection-detection assembly, and a control unit coupled to output of the measuring unit, wherein:

the illumination assembly produces incident light of substantially broad wavelengths band directed onto the structure at a certain angle of incidence, and the collection-detection assembly detects spectral characteristics of light returned from the structure and generates measured data representative thereof;

the measuring unit is operable for carrying out at least first and second measurements and generating measured data representative of the detected returned light; and said control unit is operable to be responsive to the generated measured data for analyzing the measured data obtained with the first measurement to determine at least one parameter of the structure, and utilizing the at least one determined parameter while analyzing the measured data obtained with the second measurement for determining the line profile of the structure.

The scatterometry based measurement technique provides the collection of a large amount of data from each measured profile, e.g., the diffraction efficiency in a large number of different angles or a large number of wavelengths. This richness of data may allow the fitting of the measurements to the results of a multi-parameter model describing the measured profile, thus providing more information than merely stating the CD. This additional information also provides confidence in the results, particularly if the effective number of independent measured values is significantly larger than the number of free parameters in the model. Since exact models describing diffraction from general profiles and in general situations have been developed for years and are known to be of high accuracy, these methods have a good chance of obtaining accurate results.

The system according to the invention can be applied as an integrated metrology tool. In contrast to all conventionally used off-line measurement tools, occupying a large footprint and requiring additional manual operations that slow down the entire fabrication process and allow only the measurement of samples from each production lot, the system of the present invention may be integrated as part of the production machine, thus allowing full automation of the manufacturing process. For this integration to be possible, the system should be very economical in space.

Additionally, the operation of the system is fast enough, so that every semiconductor wafer in the production line can be measured, allowing closer control over the process. The system of the present invention enables a multi-stage measurement procedure, thereby improving the quality of the entire measurement. The measurement technique according to the invention requires only a small measurement site in accordance with the area constraints, which characterize current lithography.

More specifically, the present invention is used for process control in the manufacture of semiconductor devices (wafers), e.g., the control of a lithography process, and is therefore described below with respect to this application.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

Figure 1:
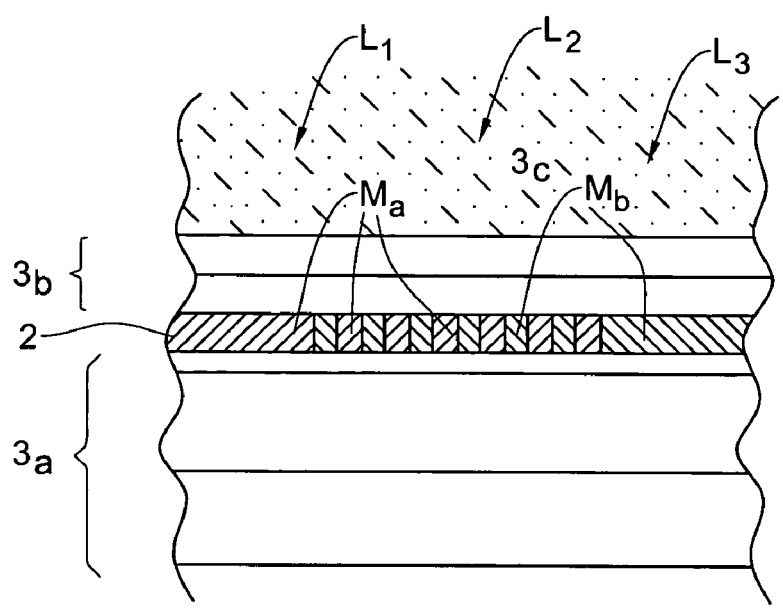
FIG. 1 is a schematic illustration of a wafer structure.

Referring to FIG. 1, there is illustrated (not in a correct scale) a wafer W that typically has a plurality of stacks formed by different layers, and presents a structure with a periodic pattern. Measurements are aimed at determining the profile of the periodic pattern ("grating") formed in one or more of the wafer's layers—layer 2 in the present example. Generally, the periodic pattern may involve more than a single layer (which are not specifically shown here), provided that the periodicity in all patterned layers is equivalent. This periodicity may be either one-dimensional (i.e. repeated lines) or two-dimensional periodicity (i.e. finite-area units repeatedly placed on the nodes of a two-dimensional grid). The patterned layer is enclosed between a plurality of un-patterned, underlying layers 3a and a plurality of un-patterned, over-lying layers 3b terminated by a background medium 3c (e.g. air).

The patterned layer 2 may include both patterned and un-patterned sites. In the un-patterned site, e.g. $L_1$, $L_3$, a single material, either $M_a$ or $M_b$, is to be found within an area larger than the area of the measurement spot. As to the patterned site, e.g. $L_2$, both materials $M_a$ and $M_b$, having different optical constants, are to be repeatedly found within the area of the measurement spot. In specific applications, materials $M_a$ and $M_b$ may take different identities. For example, both the materials of all over-lying layers and one of the materials $M_a$ and $M_b$ are identical to the background medium, .e., the measured pattern is a relief pattern. Such a relief pattern could be formed, for example, by a post-developed photoresist, or by a post-etched Poly-Silicon, Aluminum or Silicon dioxide, either stacked with photoresist or not. Examples in which none of the materials $M_a$ and $M_b$ is equivalent to the background medium may include post-exposure (undeveloped) photoresist, or "dual-damascene" type Copper lines. An example of two-dimensional periodicity would be a two-dimensional array of via-holes formed as a test pattern in order to measure the diameter and other parameters of the via-hole process.

Usually, the smallest transverse dimension of the pattern is called the "critical dimension" (CD), however other definitions of the CD may be also applied. Usually, the CD of the developed photoresist determines the CD of the patterns formed in later stages of the entire manufacturing process, thus bearing extra importance.

Figure 2A:
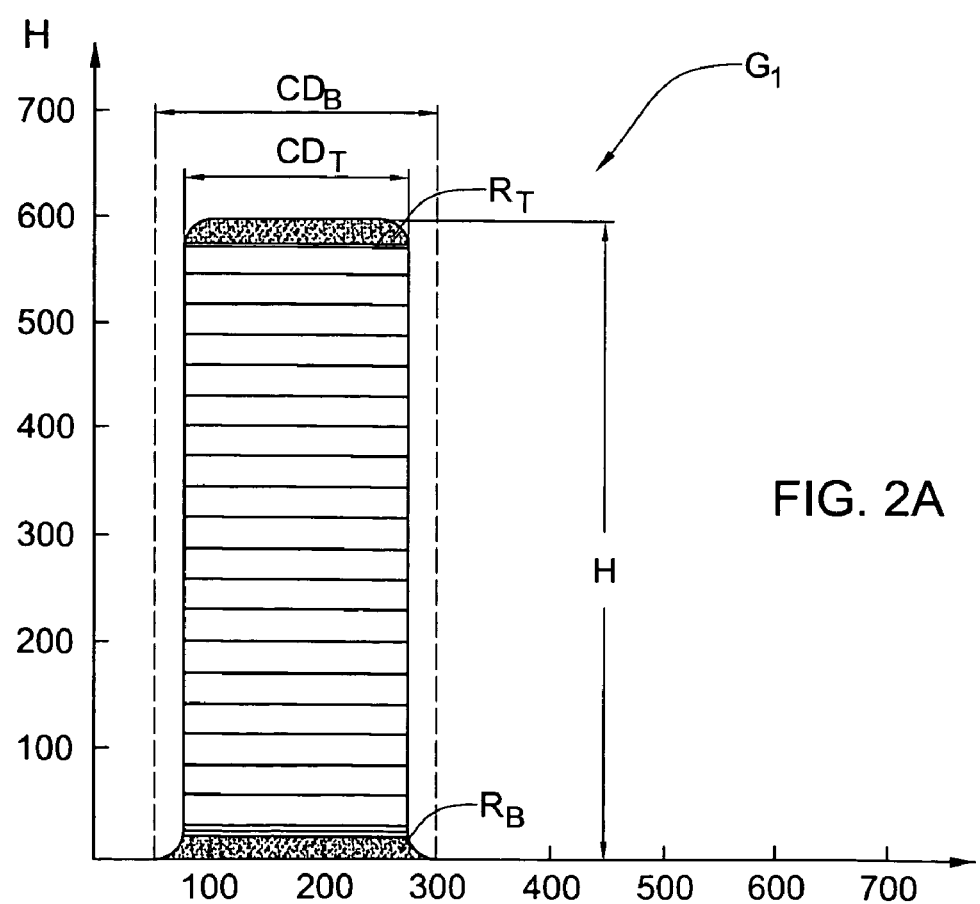
FIGS. 2A and 2B are schematic illustrations of two possible examples, respectively, of the line profile showing some parameters thereof to be measured.

The model of the periodic structure will depend on the specific application and on the requirements of the end-user. For example, FIG. 2A illustrates a graph $G_1$ exemplifying a possible model for line profile, being trapezoidal with rounded corners. In this case, the parameters to be determined may include the following:

height H of the profile G (i.e., the thickness of the photoresist);
critical dimensions $CD_B$ and $CD_T$ at the bottom and top of the photoresist region, respectively;
radius $R_B$ and $R_T$ of the curvatures at the bottom and top of the photoresist region, respectively; and
the period of grating.

Figure 2B:
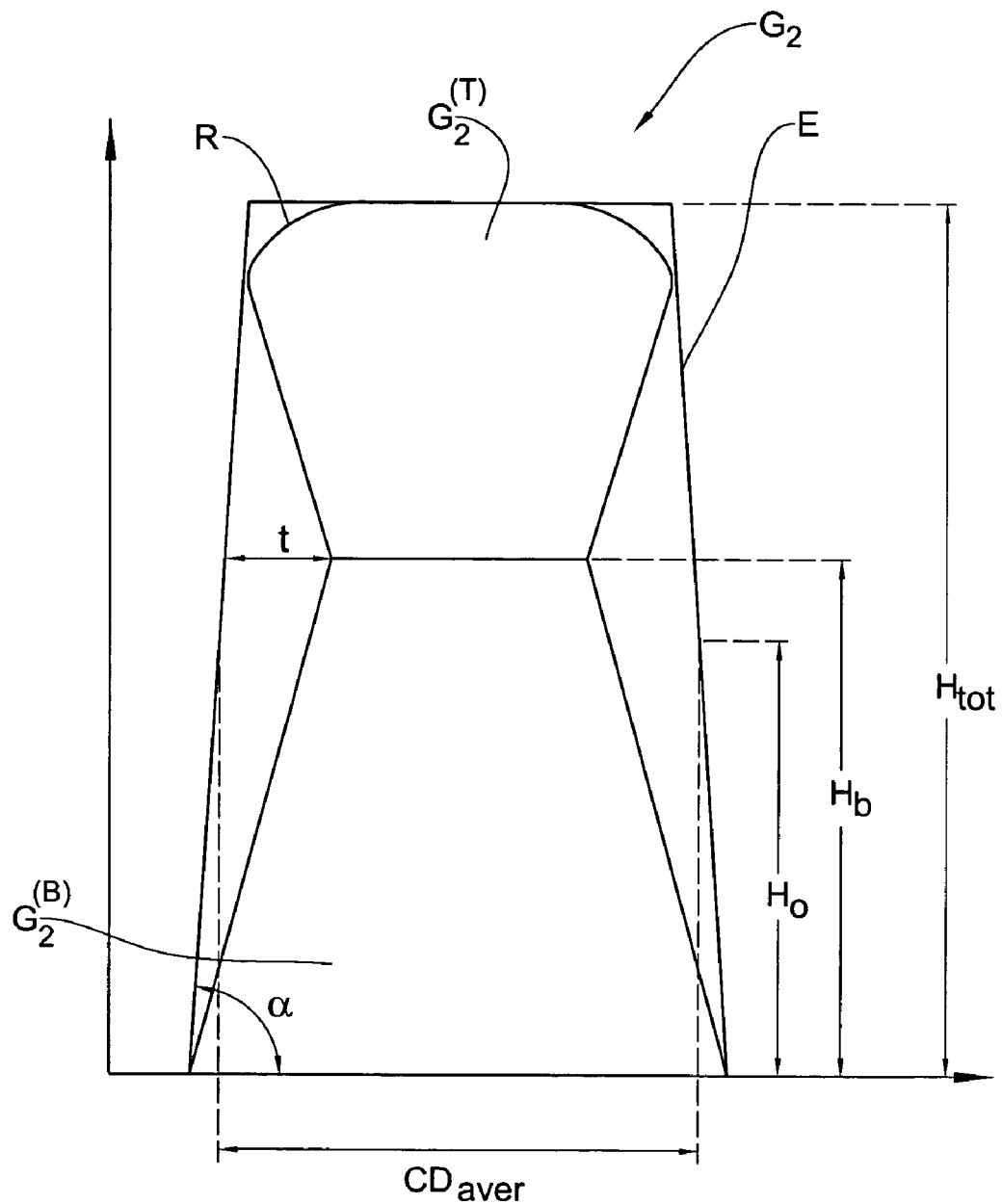

The above is the example of a symmetrical line profile. In the case of an asymmetrical profile, an additional tilt angle should also be determined. More elaborate models can also be used, e.g., by dividing the profile into several layers, each layer described by a geometric shape (e.g., trapeze), while requiring matching of the profile width in the interfaces between layers. This is exemplified in FIG. 2B showing a two-part trapezoidal line profile $G_2$ formed by top and bottom trapezoids $G^{(B)}_2$ and $G^{(T)}_2$. In this case, the parameters to be determined may, for example, include the following:

total height $H_{tot}$ of an envelope E defined by the profile $G_2$ (i.e., the thickness of the photoresist);
the average value of the critical dimension $CD_{aver}$ corresponding to the width of the envelope E at a height $H_0$ equal to the half of the total height $H_{tot}$;
radius R of the curvature at the top of the photoresist region;
the tilt of the envelope α with respect to the horizontal plane P;
the maximal distance t between the profile $G_2$ and the envelope defined thereby;
the height $H_b$ of the bottom-part trapezoid $G^{(B)}_2$; and
the period of grating.

Measurement is based on obtaining the diffraction efficiency spectrum from a grating on the wafer. The grating is any periodic structure in one or two dimensions composed of features whose parameters should be measured, e.g. line-width, through holes diameters, etc. Due to the periodic structure, the diffraction from the features on the wafer is limited to a discrete number of angles (diffraction orders), as governed by the diffraction equation:

$$\sin\Theta_r = \sin\Theta_i + n\frac{\lambda}{d} \quad (1)$$

where $\Theta_i$ is the incidence angle, $\Theta_r$ is the reflected angle, λ is the wavelength, d is the grating period and n is the order number (n=0 being the specular reflection).

It should be noted that the measured gratings could be either an integral part of the operative portion of the wafer or a test pattern. Such small test structures which are typically smaller than 40 μm×40 μm are measured using a focusing optics.

Figure 3:
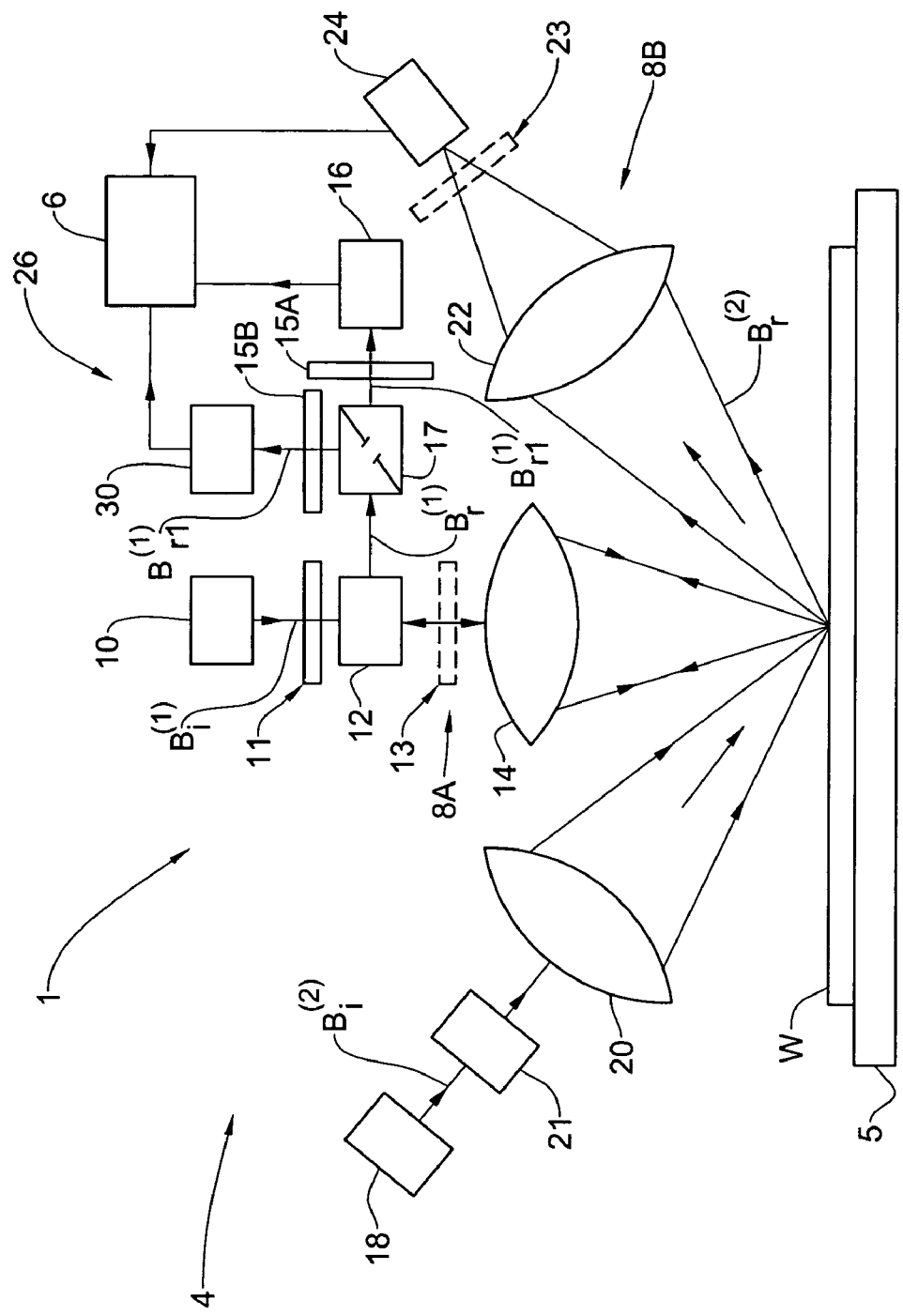
FIG. 3 is a schematic illustration of the main components of a measurement system constructed according to one embodiment of the invention.

Reference is made to FIG. 3, illustrating a measurement system 1 constructed and operated according to the invention for measuring parameters of a wafer W (constituting a patterned structure). The system 1 includes a measurement unit 4, a support stage 5 for supporting the wafer W and a control unit 6. Also provided in the system 1, is a wafer handler, which is not specifically shown. The wafer handler serves for loading/unloading wafers to and from the stage 5, and may include a suction means for holding the wafer. Generally speaking, the wafer handler and wafer stage serve together for receiving wafers from a processing tool (not shown here), pre-aligning them along coordinate axes (e.g., by rotating the handler), maintaining, placing in a measuring position and returning them to the same or another processing tool.

The measurement unit 4 defines two measurement channels, generally at 8a and 8b, respectively. Each measurement channel includes such main constructional parts as illumination and collection-detection assemblies.

The illumination assembly of the channel 8a is composed of a light source 10, for example a Xenon arc lamp, a controlled polarizer 11, a beam splitter 12 and an objective lens 14 that is driven by a suitable motor (not shown) for auto-focusing purposes. The light source 10 generates incident light $B^{(1)}_i$ of a broad wavelength band. The polarizer 11 serves to separate only light components of the desired polarization and allow its collection. The beam splitter 12 serves for spatially separating incident and returned light components. It should be noted that the polarizer could be accommodated in any point along the optical path. However, in order to avoid possible changes in the polarization state of light induced by optical elements located between the polarizer and the wafer, the polarizer is preferably positioned as close as possible to the wafer. The collection-detection assembly of the channel 8a includes a spectrophotometric detector 16 and a beam splitter 17 in the form of a pinhole mirror, the purpose of which will be explained further below. As shown, an additional polarizer 15a may be accommodated in the optical path of light ensuing from the pinhole mirror 17 and propagating towards the detector 16. In the measurement channel 8a, the incident light $B^{(1)}_i$ normally impinges onto the wafer W, and light $B^{(1)}_r$, specularly reflected (normal "0" order), is collected and directed towards the detector 16, in a manner described further below.

The illumination assembly of the measurement channel 8b is composed of a light source 18 (e.g., the same Xenon arc lamp) generating incident light $B^{(2)}_i$ of a broad wavelength band, an objective lens 20 which is similarly associated with a suitable drive (not shown) for auto-focusing purposes, and a controlled polarizer 21. The collection-detection assembly of the channel 8b includes a collecting lens 22, a spectrophotometric detector 24 and, optionally, a controlled polarizer 23 (shown in dashed lines). The incident light $B^{(2)}_i$ impinges onto the wafer W at a certain angle (e.g., 60°), and a specularly reflected light component $B^{(2)}_r$ (oblique "0" order) is detected. It should be noted that alternatively, either one of the polarizers 21 and 23 or both of them could be used in the measurement channel 8b. The provision of the polarizer, included in either one of illumination and collection-detection channels, or both is associated with the fact that diffraction efficiency is also a function of polarization, resulting in inherently different diffraction efficiency spectra in "perpendicular" polarizations. Additionally, the appropriate selection of light polarization may provide better sensitivity to parameters of the line profile. Assume, for example, that the so-called "conventional mounting" of the illumination assembly, namely such that the oblique incident beam $B^{(2)}_i$ propagates towards the wafer in a plane perpendicular to the lines of the grating. If a dielectric pattern in measured (e.g., post-developed photoresist, post-etch silicon or post-etch oxide), TE-polarization is preferred, i.e., the vector of the electric field is perpendicular to the plane of incidence and parallel to the grating lines. If post-etching measurement is performed on a metallic patterned structure, TM-polarization is preferred, i.e., the vector of the electric field lies in the plane of incidence and is perpendicular to the grating lines.

It should be noted, although not specifically shown, that optical fibers may be used for directing light components ensuing from the pinhole mirror 17 and lens 22 to the detectors 16 and 24, respectively. Hence, the detectors could be mounted at any suitable location. A suitable drive assembly is provided for moving the optical elements in the X-Y, thereby enabling the measurements at different locations on the wafer. Additionally, the wafer stage 5 is also equipped with a drive assembly (not shown), which allows for aligning the wafer along the Z-axis, rotating the wafer in the horizontal plane, and leveling the wafer around two rotational axes such that the surface of the wafer will be parallel to the X-Y plane of the optical elements. The requirement for the leveling is derived from the sensitivity of the measurements to the angle of incidence. The requirement for rotating the wafer in the horizontal plane (so-called "Θ-control") is derived from the fact that the diffraction depends on the mounting direction. Thus, in order to bring the wafer to the so-called "conventional mounting" position, this degree of freedom is required. Additionally, this degree of freedom allows for using a window that covers only a half of the wafer. Hence, the two halves of the wafer are sequentially measured by rotating the wafer by 180° with respect to the window. This concept is described in a co-pending application assigned to the assignee of the present application. Such a technique enables to save considerable foot print area which is a critical factor when using a measurement system as an integrated metrology tool.

It should also be noted that the system 1 could be provided with a dynamic auto-focusing assembly enabling high-speed measurements. Auto-focusing could be performed either with each measurement channel separately, by moving one or more of its optical elements (lenses), or with both measurement channels, using the wafer stage Z-axis control.

As further shown in FIG. 3, an additional, imaging channel 26 is provided. Channel 26 includes the illumination assembly of the "normal incidence" channel 8a, a polarizer 15b and an imaging detector 30 (e.g., a CCD camera) receiving light components reflected from the pinhole mirror 17.

The polarizers 15a and 15b are used in the collection-detection assemblies of the measurement channel 8a and imaging channel 26. Alternatively, a single polarizer 13 (shown in dashed lines) could substitute the polarizers 11, 15a and 15b. While, the option of using the single polarizer 13 is more economical in price and space as compared to the option of using three polarizers 11, 15a and 15b, the use of three separate polarizers allows for measuring in the preferred polarization whilst observing the wafer surface with the imaging channel through perpendicular polarization. This configuration, called "Nomarski", is similar to dark-field configuration in the sense that the pattern edges are strongly enhanced in the image, thus allowing for better, more accurate pattern recognition in some cases. The polarizer 15b in the imaging channel 26 could thus be mounted for rotation so as to change its preferred polarization, or for shifting between its two operational positions so as to be in or out of the optical path, per user's choice.

The main principles of the construction and operation of a measurement system including the zero-order detection spectrophotometer (measurement channel 8a) and the imaging channel 26 is disclosed in U.S. patent application Ser. No. 08/497,382, assigned to the assignee of the present application. This document is therefore incorporated herein by reference with respect to this specific example.

The pinhole mirror 17 separates a central part $B^{(1)}_{r1}$ (about 20 μm) of light $B^{(1)}_r$ specularly reflected from the illuminated spot and collected by the lens 14, and allows its propagation towards the spectrophotometric detector 16. A periphery part $B^{(1)}_{r2}$ of light $B^{(1)}_r$ is reflected from the mirror 17 towards the imaging detector 30. As a result, the measurement area, considered in the spectrophotometric detector 16, presents a "dark" central region, typically 40 μm in diameter, in the center of the field of view of the imaging channel, typically being 20 mm×20 mm, both measured on the wafer. This approach enables to locate the measurement area in the entire illuminated spot defined by the field of view of the CCD.

The outputs of the spectrophotometric detectors 16 and 24 and the imaging detector 30 are coupled to the control unit 6. The control unit 6 is typically a computer device having a memory for storing reference data (libraries), one or more processors for analyzing data coming from the detectors and controlling all the operations of the measurement system 1 including driver(s), light sources, power supply, interface, etc. The preparation of libraries will be described further below. The control unit 6 also displays the measurement results. The processor is operated by suitable image processing and pattern recognition software, capable of both global and site-to-site alignment. The alignment technique based on the features of the pattern is disclosed in U.S. Pat. Nos. 5,682,242 and 5,867,590, both assigned to the assignee of the present application. Thus, the control unit 6 is capable of locating and processing measurements. The analysis of the measured data could be used for establishing feedback closed-loop control of a corresponding processing tool, as will be described further below.

Another feature of the present invention consists of the optional use of a second spectrophotometer for calibrating the light sources' spectra. It is known that several types of light sources have spectral characteristics varying in time. Thus, any previous measurement (calibration) of the incident spectrum will lead to significant errors in interpretation. By taking a known fraction of the incident light (e.g., in channel 8a, the signal reflected by the beam splitter) and measuring its spectral characteristics simultaneously with the measurement of the diffraction signal, this problem can be avoided. Alternatively, a photodiode whose output has been previously learned could be used to calibrate for intensity variations, assuming the relative spectrum to be constant.

Figure 4:
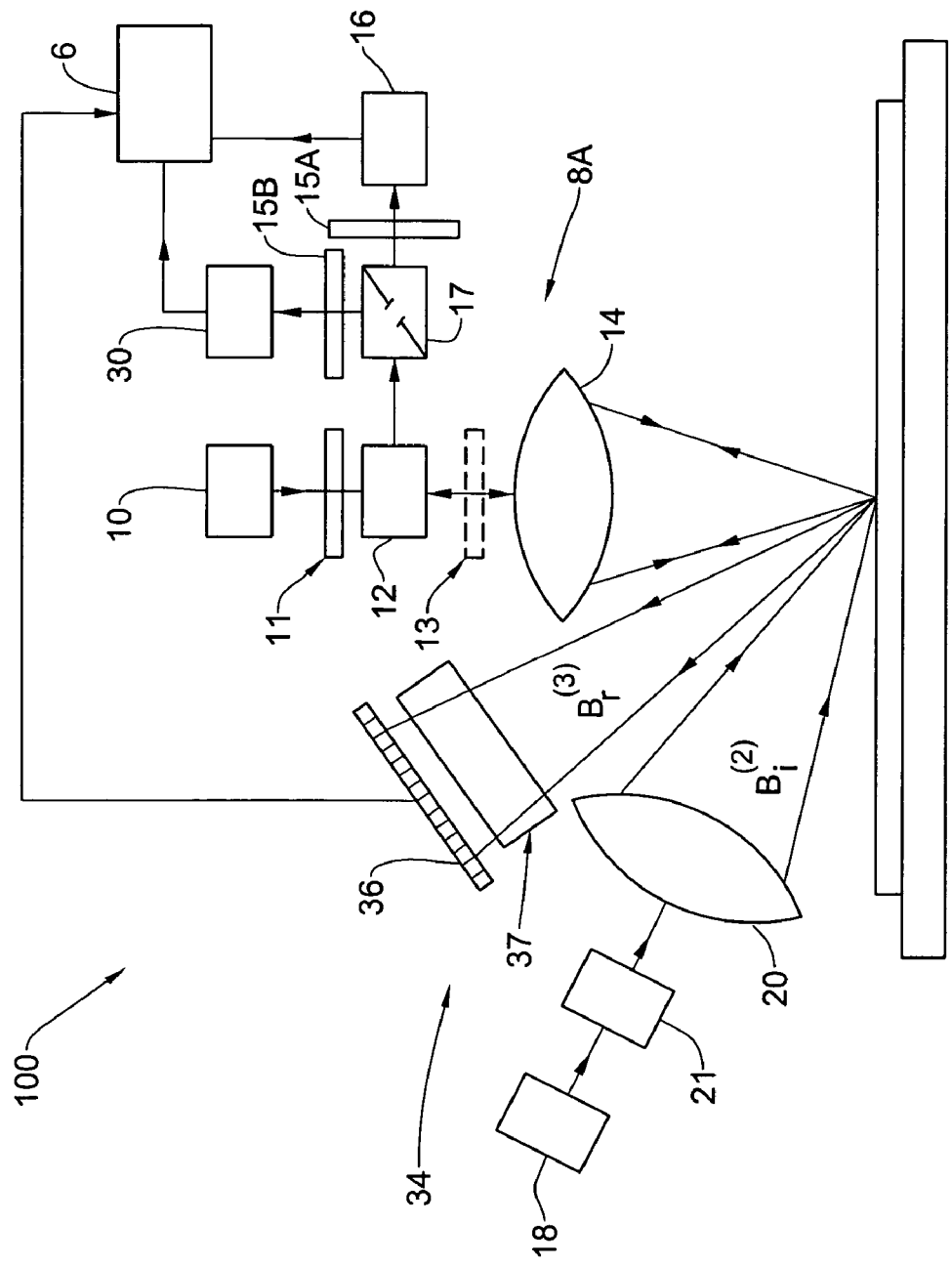
FIG. 4 is a schematic illustration of the main components of a measurement system constructed according to another embodiment of the invention.

Reference is made to FIG. 4 illustrating a measurement system 100, constructed and operated according to another embodiment of the invention. To facilitate understanding, same reference numbers are used for identifying those components which are identical in the system 1 and 100. In the system 100, a measurement channel 34 collecting a light component of "−1" diffraction order is provided instead of the oblique "0" order measurement channel 8b. The illumination assembly of the measurement channel 34 includes the light source 18, the polarizer 21 and the objective lens 20, while its collection-detection assembly includes a linear detector array 36, for example, a plurality of photodiodes and an optical light guiding assembly 37 (e.g., fiber bundle, set of prisms or combination of both). Here, each of the lenses is of a small numerical aperture (NA=0.1) providing the angles of light propagation within a range of ±5°. In this specific example, the angle of incidence of the light component $B^{(2)}_i$ is about 60°, and light components $B^{(3)}_r$, being the "−1" order of diffraction from the wafer propagate within a large solid angle, e.g., 50°, and are collected by the linear detector array 36. The optionally provided light-guiding assembly 37 serves for transferring the light diffracted in the "−1" order from the vicinity of the wafer W to a remote location of the detector array 36, thus allowing some flexibility in its location.

The measurement channel 34, in distinction to the channel 8b, does not need a spectrophotometer. Indeed, the photoresist grating already disperses the light diffracted in the "−1" order, and therefore there is no need for any additional dispersive element in the system. However, it is also possible to use the light-guiding assembly for focusing light collected at the "−1" order to the entrance of a spectrophotometer, thus converging and re-dispersing the optical signal. This configuration together with an appropriate switching device (not shown) will eliminate the use of the special detector array 36 for detecting the "−1" order by using the same spectrophotometer 16 for sequential measurement of both "0" and "−1" orders. The use of one or more switching devices of the same kind would allow the utilization of a single spectrophotometer for all the measurement channels 8a, 8b and 34.

It should be noted that if the resulting signal is not sufficiently strong, a cylindrical lens (anamorphic optics) could be used to concentrate more energy onto the detector. Additionally, in order to detect the spatial distribution of different wavelengths within the solid angle corresponding to the "−1" diffraction order, an appropriate calibration procedure is previously carried out, for example, by using spectral filters, or by finding spectral peaks of the light source using a calibration target having sufficiently smooth diffraction efficiency in a spectral region around the peaks.

Turning back to the diffraction equation presented above, the configuration of FIG. 4 allows for collecting, for example, the following wavelength ranges: (a) in the case that d=0.36 µm, 344 nm<λ<606 nm, or (b) in the case that d=0.26 µm, 248 nm<λ<438 nm, both cases correspond to $\Theta_r=(-5°)-(-55°)$.

The above wavelength ranges are, on the one hand, sufficiently wide (i.e., $\lambda_{max}/\lambda_{min}=1.76$) and substantially outside the DUV region, and, on the other hand, approach the following condition: λ=d. This allows for meaningful information to be gained.

Figure 5:
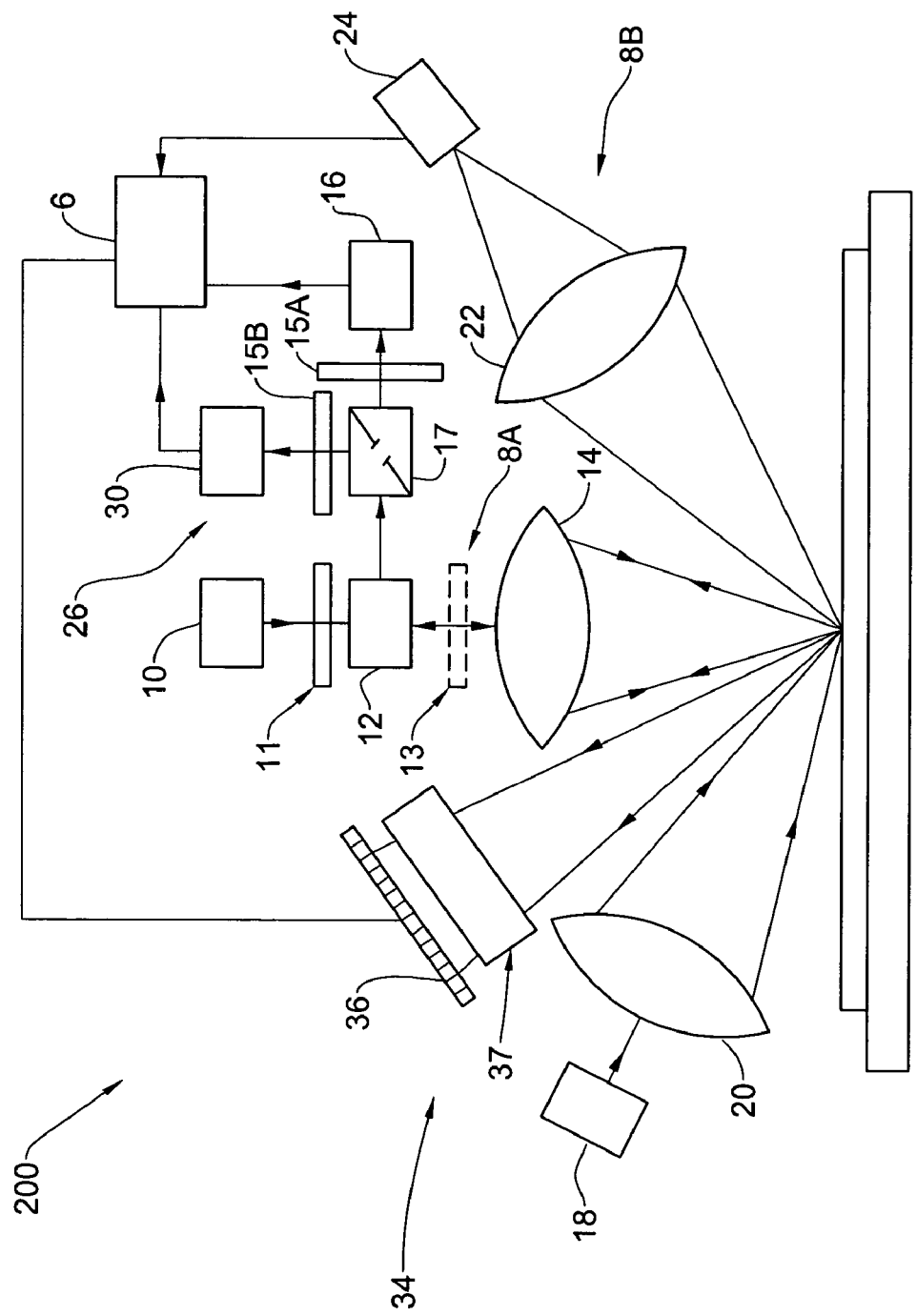
FIG. 5 is a schematic illustration of the main components of a measurement system constructed according to yet another embodiment of the invention.

FIG. 5 illustrates a measurement system 200 which includes three measurement channels—channel 8a (normal "0" order), channel 8b (oblique "0" order) and channel 34 ("−1" order), and the imaging channel 26. For simplicity, the different polarizers are not shown here. This configuration combines the measurement channels of the systems 1 and 100, thus increasing the amount of obtainable information.

Figure 6:
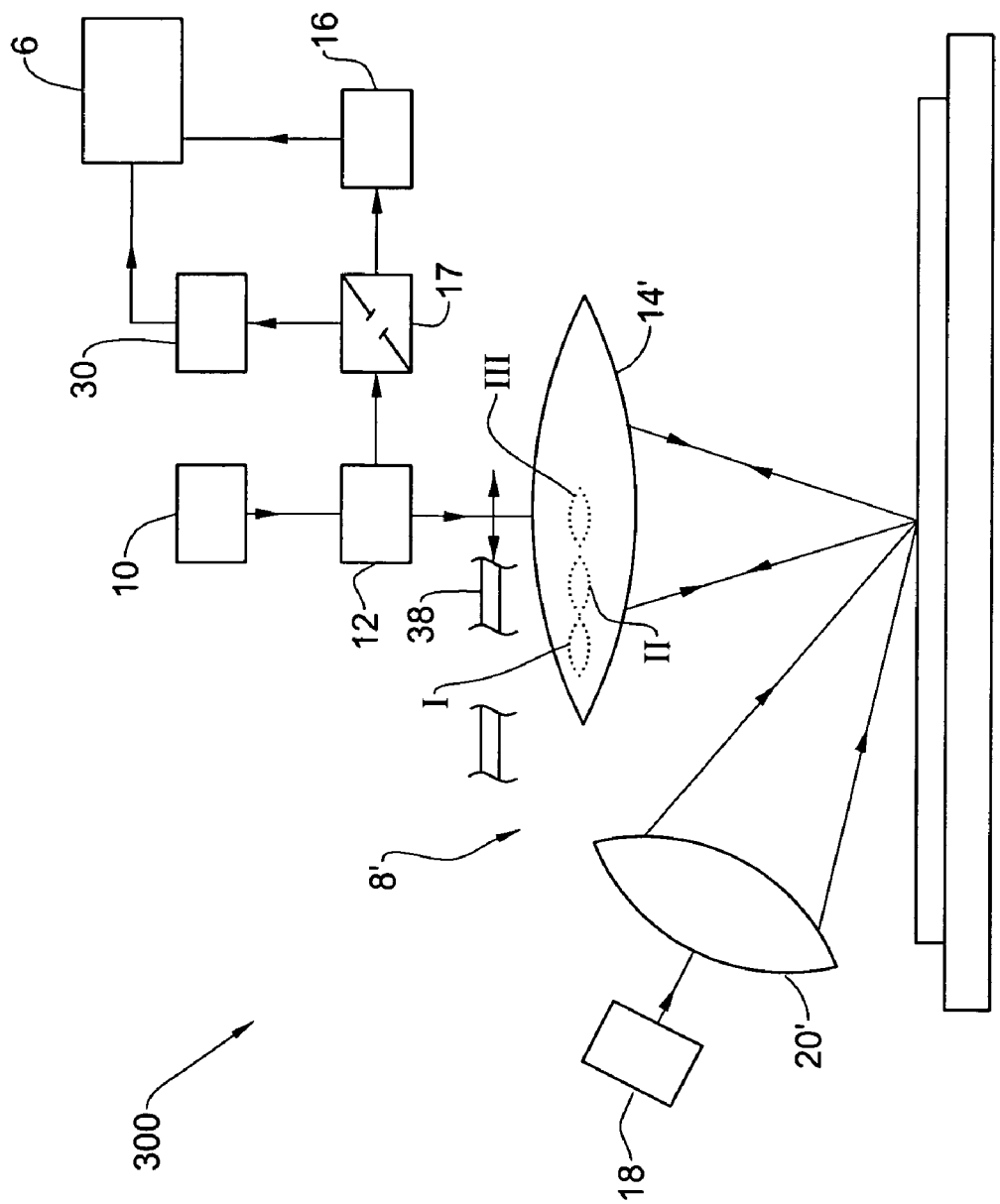
FIG. 6 is a schematic illustration of one more embodiment of the invention.

Referring now to FIG. 6, there is illustrated a measurement system 300, where the collection-detection means of the normal "0" order" and "−1" order form a unified collection channel 8', utilizing a common objective lens 14' and a common spectrophotometric detector 16. To this end, both lens 14' and lens 20' have a larger numerical aperture, as compared to their counterparts in the previously described systems. An aperture 38 is provided, being mounted for movement along the lens 14' in a plane parallel thereto. Each location of the aperture 38 (locations I, II and III in the present example) "opens" only a small part of lens 14'. Thus, at each position of the aperture 38, only light components propagating within a solid angle defined by the aperture, and therefore being only a small part of the entire solid angle covered by lens 14', are directed towards the detector 16. Since the diffraction angle $\Theta_r$ in non-zero orders is determined by both the incidence angle and the wavelength, and through the diffraction equation (1) above, fixing the diffraction angle means that the incident angle is a function of the wavelength. For a fixed collection angle $\Theta_r$ and n=−1, one thus has:

$$\Theta_i = \arcsin\left[\sin\Theta_r + \frac{\lambda}{d}\right] \quad (2)$$

The obtained spectrum is thus inherently different from those obtained by prior art techniques, since, in distinction to these techniques, neither the angle of incidence nor the wavelength is fixed. The measurement system according to the present invention allows for a multiplicity of diffraction angles $\Theta_r$, and for increasing the amount of information that can be collected, as well as the accuracy and reliability of the results.

As to the normal "0" order, it is successfully collected when the aperture 38 is shifted so as to be centered with the optical axis of the lens 14' (position III), and illumination from the light source 10 is used instead of that of the light source 18.

Figure 7:
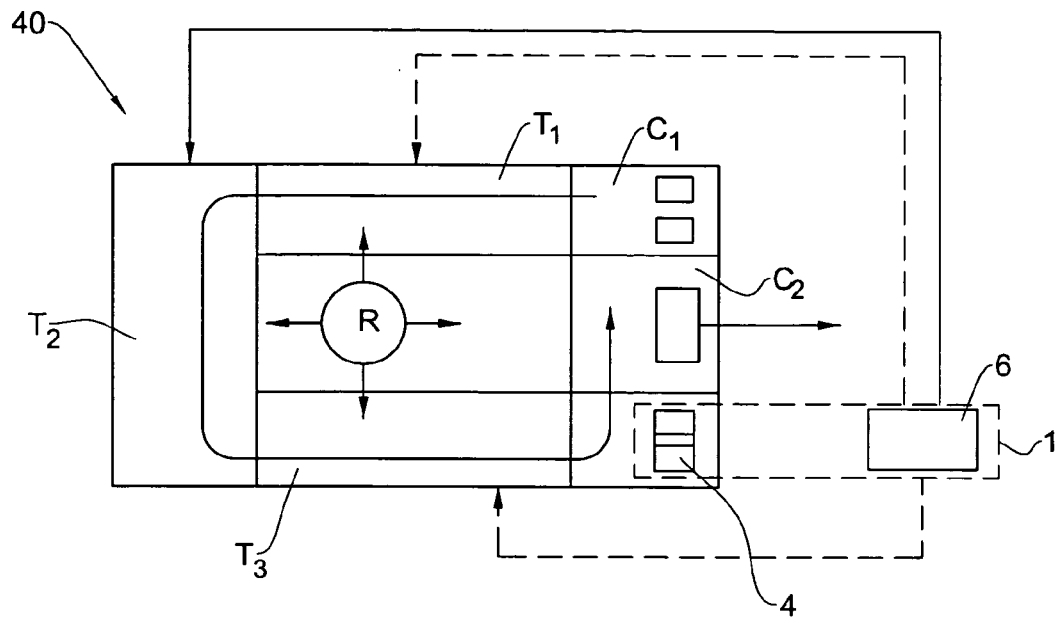
FIG. 7 is an example of a part of a production line utilizing the system of either of FIGS. 3, 4, 5 and 6.

Reference is made to FIG. 7, showing a part of the wafers' production line utilizing the measurement system of the present invention. Here, the measurement system, for example the system 1, is associated with a lithography arrangement 40. This arrangement 40 typically includes coater, exposure and developer tools $T_1$, $T_2$ and $T_3$, loading and unloading cassette stations $C_1$ and $C_2$, and a robot R. The construction and operation of such a lithography arrangement are known per se, and therefore need not be specifically described.

In the present example, the system 1 is integrated with the arrangement 40, and is accommodated in a manner allowing its application to a wafer ensuing from the developer tool $T_3$. The control unit of the invented system is coupled to a control unit of the exposure tool $T_2$ (not shown) for feedback purposes, for example for adjusting the exposure dose/time, focusing, etc. It should, however, be noted that the system 1 could also be coupled to the coater and/or developer tool for adjusting their parameters (e.g., photoresist thickness, post-exposure baking time, development time, etc.) prior to processing the next coming wafer. As for the measured wafer, it can be returned for reprocessing, if needed.

It should also be noted that data indicative of the wafer's profile can be used for adjusting the parameters of an etching tool prior to its application to the measured wafer or the next coming wafer, i.e., for feed-forward purposes. Alternatively or additionally, the measurement system can be used for post-etching measurement.

Figure 8:
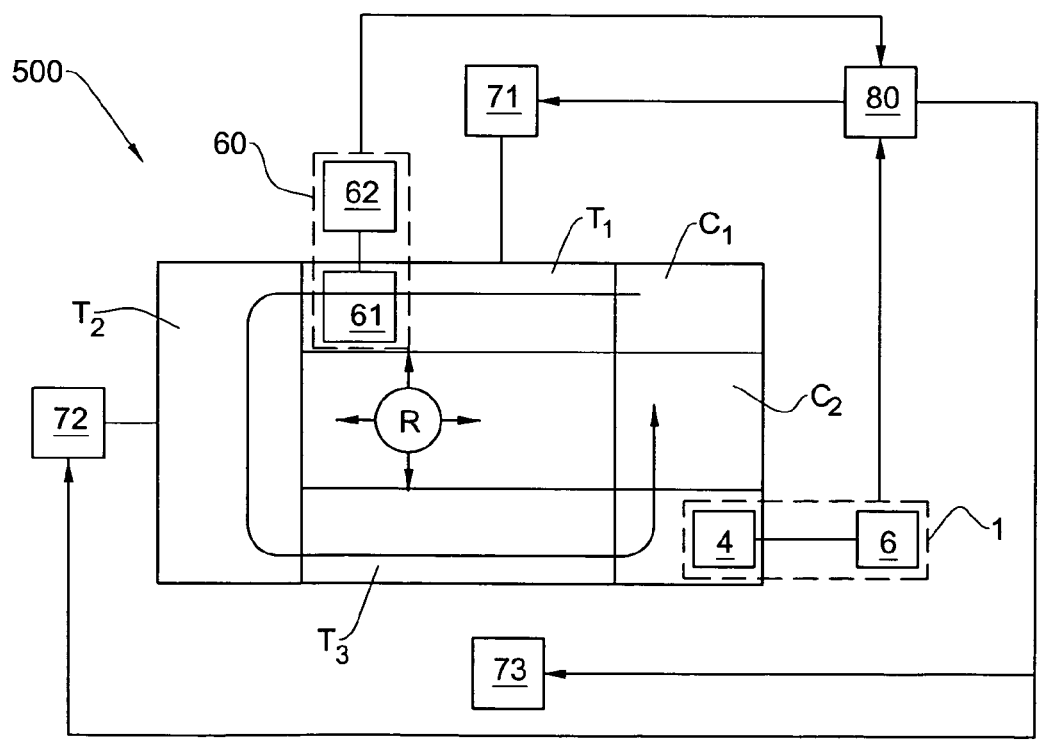
FIG. 8 illustrates another example of a production line utilizing the system of either of FIGS. 3, 4, 5 and 6.

FIG. 8 shows another example of a production line utilizing the measurement system of the present invention, for example the system 1. Here, the measurement system is integrated into a complete CD control system 500. The system 500 includes the following components:

- a system 60 for measuring the parameters of the photoresist and of the under-lying layers prior to exposure, which system is composed of a measuring unit 61 and a control unit 62;
- the system 1 for measuring CD and other profile parameters, which system comprises the measuring unit 4 and the control unit 6;
- a set of controllers 71, 72, 73 for controlling tools $T_1$, $T_2$, $T_3$, respectively, of the lithography arrangement; and
- a system controller 80.

The main idea of the system 500 is that information from both pre-exposure and post-develop stages is combined, allowing for a complete closed-loop-control utilizing both feedback and feed forward. The operation of the system 500 is mainly guided by the controller 80, which receives information from both systems 60 and 1. An expert system, which is a learning software tool running on the controller 80, accumulates the information from different measurements (across the wafer, wafer to wafer, etc.) and learns the correlation between pre-exposure and post-develop measurement. The expert system also learns the effectiveness of using different control parameters related to tools $T_1$, $T_2$, $T_3$, in the reduction of variations in the resulting CD and the methods to combine them in the most effective way.

One of the features, that the system 1 (or similarly systems 100, 200, 300) will require in order to be effectively integrated into the system 500, is OCR (optical character recognition) capability for identifying each wafer by its identity number. Identifying the wafers in a deterministic way is important for the reliability of the system controller 80, as well as for the integration of system 500 with post-etch measurements carried out on other processing tools in the fab through a common communication network or database. OCR capability could be achieved either by scanning the area containing the identity number using the X-Y stage and the viewing channel 26, or, alternatively, by a special OCR channel (which is not specifically shown). Such an OCR channel may include a CCD camera, imaging optics, and a controller running OCR software.

The operation of the measurement system according to the invention will now be described. Setup of the measurement includes the following two stages:

1) Definition by the user of a profile model to be used and ranges for each parameter of the selected model. Additionally, knowledge about all the layers in the wafer and their optical properties, and any additional relevant information concerning the product (wafer) to be measured and/or the measurement conditions, is desired for defining the measurement sites.

2) Preparation of a library of spectra (reference data) corresponding to all the possible profiles. Each spectrum in the library provides the diffraction efficiency for a given profile of the grating, given polarization, given angle of incidence and mounting method, given numerical aperture of the system, and a given diffraction order as a function of wavelength.

An important feature of the present invention refers to the fact that one has to take into account the finite numerical aperture of the system. This numerical aperture, required for measuring small sites, means that light is incident on the wafer at a considerable range of angles at the same time. Since diffraction efficiency is a sensitive function of the incident angle, failing to consider this fact will result in significant error. In order to take this effect into consideration, one can calculate the diffraction efficiency from each profile at several angles of incidence around the central one (i.e., the average direction of the solid angle of light propagation). Then, the weighted average of diffraction efficiency spectra at the different angles will be calculated in order to obtain the effective diffraction efficiency for the entire cone (solid angle) of angles of incidence. For example, in a system having the central angle of incidence equal to 60°, the diffraction efficiency corresponding to 57°, 60° and 63° angles of incidence could be calculated, and then weighted with respective weights of 0.25, 0.5 and 0.25. The fact that a small number (e.g., three) of such angles is sufficient to describe a continuum of angles is not trivial, and the selection of the number, spacing and averaging of the different angles may be application dependent.

The calculation is made using the known Rigorous Couple Wave Analysis method, modal methods, or by a hybrid method containing parts of both previous methods.

The preparation of the library may be made in one or more stages. For example, the following scheme may be used:

(1) Initially, the spectra corresponding to a small number of profiles only are calculated, sparsely sampling the whole multi-dimensional space of possible profiles.

(2) At this point, several measurements are taken and analyzed using the initial library. Approximate average values of the desired parameters are then determined, describing an approximate average profile of the grating.

(3) A sub-space of possible profiles is defined around the average profile. The sub-space is sampled with the required (final) resolution, and the spectra of all profiles in the sub-space are calculated. Alternatively, the spectra in the sub-space can be calculated "upon request", i.e., when required for the interpretation of consecutive measurements.

(4) The rest of the profile space is divided into sub-spaces with increasing distance in the parameter space from the average measurement.

(5) These sub-spaces are consecutively sampled and their corresponding spectra are calculated until the whole parameter space is calculated in the final resolution.

The advantage of the above scheme is that the continuous measurement can start already after step (3) thereby significantly saving the setup time. In fact, the above-described dynamic process of the library preparation allows to operate the system almost immediately after the recipe is prepared. Initially, the system will support only a reduced throughput, since it will have to rely mainly on slow, real-time spectrum calculations. At this stage, only some of the wafers will be measured on-line, while others will be measured, but their results will either be stored for later interpretation (if needed) or interpreted with a very low accuracy, using the crude initial library. With time, the system will support higher and higher throughput, since most of the relevant parts of the spectral library will be ready, until the maximal throughput is obtained when the whole library is prepared.

Additionally, in distinction to alternative techniques, in which the system has no independent ability to prepare a library on-site, the above dynamic scheme advantageously has the possibility of handling variations in optical constants. It is well possible that over time, the optical constants of some layers will change slightly. This change could result from lot-to-lot variations due to the changes of the properties of photoresist (e.g. composition) or slight changes in process conditions (e.g. temperature, humidity). The chemical producer may disregard such changes since they are not supposed to have any direct effect on the process (e.g. changes in the optical constants of photoresist at wavelengths different from the exposure wavelength). On the other hand, any change in the optical constants of the measured layers will obviously have an effect on the measurement with the measurement system (1, 100, 200, 300). In order to avoid this problem, the system has to monitor on a continuous basis the optical constants of the layers, and, in case that these deviate significantly from the constants used for the calculation of the library, the library has to be rebuilt. If the changes in the optical constants are sufficiently smooth, a system with on-board computational power will be able to follow the changes without a significant deterioration in the measurement accuracy. Obviously, any technique that relies on external computational power will be disadvantageous in the scenario.

As an alternative to geometrical profile models (e.g. trapeze), the profiles to be used for the preparation of the spectral library could be obtained through simulation of the relevant process. This is in contrast to the above technique of producing possible profiles that has no a-priori connection to the real process. For example, if the patterned layer is developed photoresist, than simulation of the lithographic process may be used to obtain expected line profiles from input parameters such as resist thickness, absorption coefficient, sub-layer reflection, exposure wavelength and doze, and parameters of the exposure system, such as numerical aperture and focus conditions. In this case, each set of such input parameters will result in a corresponding expected profile, and the preparation of the spectral library will include an additional step. The required steps thus are as follows:

(a) The user defines the type of process, type of model and the required input parameters, describing the situation prior to the process and the range of possible parameters for the process;

(b) Simulation of the process is used to produce a large set of possible profiles according to some or all possible combinations of process parameters and uncertain parameters of the structure prior to the process;

(c) An optical model is used to produce the expected spectrum for each profile according to experimental conditions of the measurement (incidence angle, numerical aperture etc.).

Step (c) of this preparation process (and the following fitting process) does not depend on the way the initial profiles have been prepared. A clear advantage of using a process-related method for profile preparation is that a greater variety of inherently different profiles can be used, thus the chances of finding the real profile are increased. Additionally, by providing the input parameters used for the simulation of the profile in addition to the actual profile, the system may provide more ready-to-use information to the user, and may possibly indicate the source of deviations found in the process.

Measurement Procedure

Step 1. Alignment of the wafer 2 is performed by the wafer handler and wafer stage, so as to provide the correct position and orientation of the wafer with respect to the measurement system 1. Alignment is controlled by feedback from position and angle sensors typically provided in the measurement system, as well as from the imaging channel 26. The alignment procedure is a very important stage of the entire measurement process, since diffraction efficiency is also a function of the angles between the incidence beam, normal to the wafer's surface and the direction of the grating.

Step 2. The first measurement site is found. This is implemented by providing a relative displacement between the objective lens (and possibly other optical elements) and the wafer along two mutually perpendicular axes within a plane parallel to the wafer's surface. For this purpose, feedback from images of some parts of the wafer acquired by the CCD camera 30 can be used.

Step 3. The measurement of reflection coefficient spectrum is carried out with the measurement channel 8a ("normal incidence "0" order") applied to one or more so-called "unpatterned site". Turning back to FIG. 1, such sites $L_1$, $L_3$ are located where there is no lateral variation within an area larger than that of the measurement spot of the measurement channel. These measurements enable to determine the thickness, reflectivity and optical constants (refraction index and extinction coefficient, n and k) of one or more layers including the patterned layer 2.

Step 4. The relative location between the wafer 2 and the incident beam $B^{(1)}_i$ is changed (e.g., by moving either the support stage or the optics of the measurement system) to a further measurement site $L_2$ having a required grating structure (a patterned site, as described above). Measurement of the reflection efficiency spectra is carried out with the "normal incidence" measurement channel 8a, in one or more polarization states. These measurement can be later utilized to extract parameters such as the thickness of the patterned layer 2, grating parameters, and optionally also optical constants.

It should be noted that generally, steps 3 and 4 could in some cases be combined, namely the above parameters of one or more underneath layers could also be determined at step 4, whilst measuring in the photoresist region by the measurement spot less than the dimensions of this region. In other words, the determination of the parameters of the patterned layer and those of one or more underneath layers could be carried out at such measurement site(s) and with such measuring conditions, that the spectral characteristic of light returned from the measurement spot is not significantly affected by the line profile.

It should, however, be noted, that, if the optical constants of a patterned layer are known or could be considered to be stable for some bunch of wafers (lot), the "normal incidence" measurement channel and the "oblique incidence" measurement channel could be applied to the same site(s) $L_2$. The measurements are preferably separated in time. Such a technique is time saving, since it eliminates the need for additional movements from the "unpatterned" site to the "patterned" site.

Step 5. Measurement of the reflection efficiency spectra is carried out at the oblique incidence in one or more diffraction orders (i.e., "0" and/or "−1" order), with the measurement channels 8b and/or 34, respectively, or in the case of system 300 through the unified measurement channel 8'. These measurements are applied to patterned sites $L_2$ as defined above (FIG. 1). Measurements can be taken from one or more grating structures per measured die, where different gratings may have different line/space ratios in order to simulate different conditions of the controlled process.

The Analysis of Measured Data

Step A: Initially, the normal incidence measurements (steps 3-4, or step 4 only) are analyzed to extract the above parameters of one or more underneath layers and of the photoresist layer, and to determine the thickness and optionally optical constants of the photoresist layer. Some of these measurements, e.g., yielding the optical constants n and k, can be carried out only once per several measurements of step 5 above, namely once per wafer, once per lot, etc.

Step B: The spectral characteristics measured with either one of the "oblique incidence" channel 8b (step 5) and the "normal incidence" channel 8a (step 4), or both are compared to the corresponding reference data, i.e., spectra stored in the library, and a so-called "best-fitting" between the measured and reference data is found. In this step, the results of the previous step are used to limit the scope of the search, thus reducing computation time. Having found a sufficiently good fitting for all the spectra, one can conclude that the measured structure has a profile most similar to that with which the "best-fitting" spectra have been determined, and can output the parameters of this profile.

By carrying out the analysis in the above two steps A and B, the problem of finding the best fitting profile is significantly reduced. This reduction is gained by de-coupling some of the parameters, e.g., heights, thus reducing the number of independent parameters in step B above. Since finding an optimum in a multi-parameter space is a problem whose complexity considerably increases with the number of independent parameters (dimensions), the de-coupling results in a faster, more accurate and more stable solution.

Several algorithms are required for the interpretation of the measured data (after the spectral library is prepared). Analysis of the layer(s)' thickness is based on algorithms utilized in NovaScan System (commercially available from Nova Measuring Instruments Ltd.) and may also apply other algorithms, for example an analysis of the optical properties of the semiconductor layer(s) utilizing a technique disclosed in U.S. Pat. No. 4,905,170 with some modifications. The fitting of the measured data to the reference data (i.e., spectral library) utilizes known statistical multivariate techniques such as Neural Networks, genetic algorithms, etc.

In a FAB for the wafers' manufacture, several concurrently operated production lines are usually utilized, which perform either the same or different manufacturing steps. Consequently, several measurement systems constructed and operated according to the invention could be installed within these production lines. In this case, the control units of the different measuring systems can be associated with a local area network (LAN), with a common server utility installed outside the production line, and possibly remote from the FAB being connected to the LAN through the computer network, e.g., the Internet. It is also possible that a common server utility is associated with control units of different measurement systems installed at different FABs.

Figure 9:
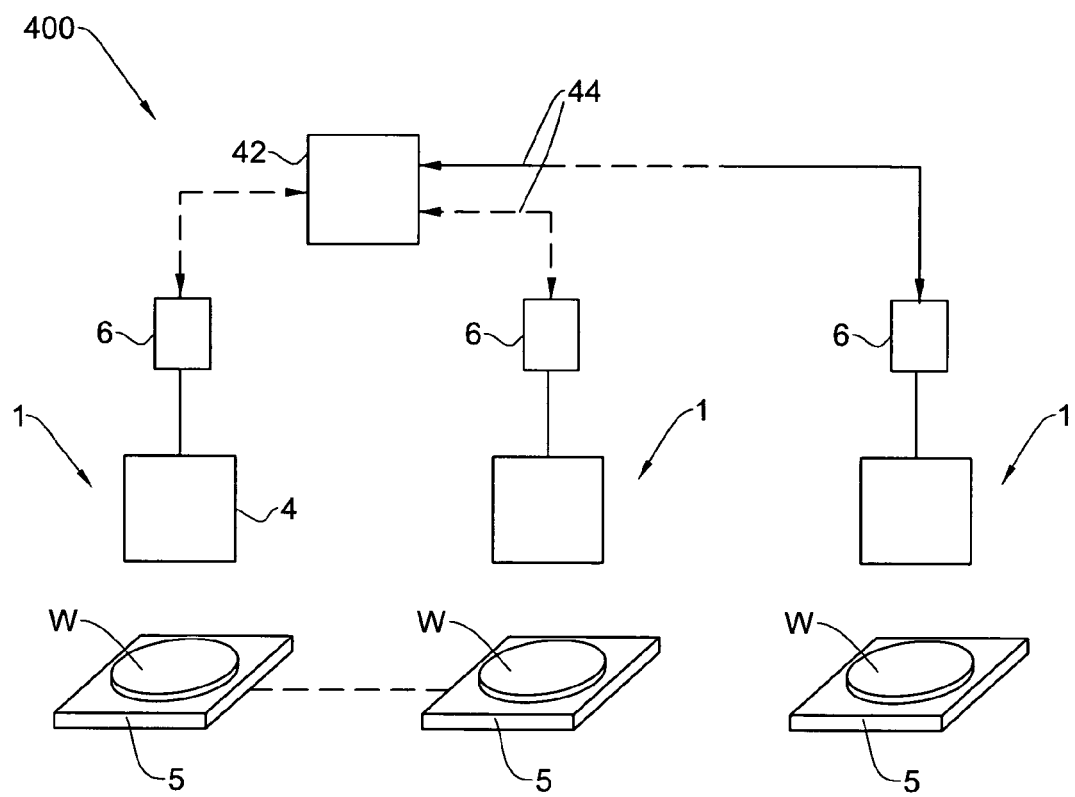
FIG. 9 is a schematic illustration of a system utilizing several measurement systems according to the invention using a common server utility.

FIG. 9 illustrates a measurement system 400 based on the above concept. The system 400 is composed of several measuring modules, each constructed similarly to either one of the systems 1, 100, 200 and 300 (system 1 being shown in the present example). Thus, each such measuring module 1 comprises the measuring unit 4, applied to the wafer progressing on a corresponding part of the production line.

As illustrated in FIG. 9, the system 400 includes a server utility 42 and several measuring modules, e.g. system 1, connectable to the server 42 through a communication link 44. The server 42 is a central processor of the entire system 400, and may perform different tasks at different operational steps. The communication network serves for connecting the server 42 to the measuring modules 1, providing the connection between the measuring modules 1, as well as connection between the server 42 and a host machine (not shown) of the FAB to enable the closed loop control of a corresponding processing tool.

During the setup of measurement, the server 42 is responsible for receiving information from the user and preparing reference data (libraries of possible models). The reference data is then transmitted over the communication network to the corresponding measuring module 1.

During the measurement procedure, the server 42 may perform the following tasks:

1) Monitor the operation of the measuring module 1 in the system 400. This utilizes both the receiving of signals from sensors, that monitor internal parameters of the measuring module (e.g. temperature, light source parameters, etc.), and generating an alarm signal in case of malfunction or evidence for required preventive maintenance.

2) Display measurement results of any one of the measuring modules to the operator. The displayed information may include the statistical analysis of any sub-group of results (e.g., in-wafer statistics, wafer-to-wafer statistics, lot-to-lot statistics, module-to-module statistics, etc.).

3) Perform all or part of the interpretation of the measured data. For example, the machine-specific calculations, such as normalization to calibration data, could be made in each measuring module, while the comparison between measured spectrum and reference data could be carried out at the server.

During the maintenance procedure, the server may display the sensors' output, perform the remote control of various mechanisms and provide on-line assistance ("help interface").

The preparation of the reference data (libraries) may be carried out by any suitable technique, for example as follows:
Preparation by the server 42 only;
Preparation by each control unit 6 separately, as described above with respect to the operation of the system 1;
Parallel preparation by several control units associated with different measuring modules connected to the same network;
Preparation by a distant server connected to the local server 42 or directly to the control units 6 through the network, e.g. the Internet.

The advantages of the present invention are thus self-evident. Measurement is carried out in both normal and oblique "0" orders, and may be measured both in "0" and "−1" orders. Thus, a wealth of data is measured which can result in more accurate reconstruction of the profile. Since the "−1" order light is that diffracted by the sample grating, it is possible to place a detector array and measure the diffracted signal directly as it comes from the wafer.

The analysis is carried out in several steps, using first the most sensitive measurement channel to measure each parameter before final optimization, and is done using data from all channels. This method reduces the possibility of finding a local minimum of the fitting function, which is not the correct profile.

The analysis is carried out using a Genetic Algorithm or another technique that does not depend on a training stage, in which the system learns from calibration examples. This increases the chances for correct measurement, and reduces the setup time.

The system allows for the measurement on small test structures (typically smaller than 40 µm×40 µm) utilizing focusing optics. The fact that a significant angle range is used is taken into account in the computation to avoid misinterpretation. The system is designed in a way that will enable its incorporation into a closed loop control system for controlling CD.

Those skilled in the art will readily appreciate that various modifications and changes can be applied to the embodiments of the invention as hereinbefore exemplified without departing from its scope as defined in and by the appended claims.

What is claimed is:

1. A measurement system configured to determine a critical dimension and a layer characteristic parameter of a structure during production, the system comprising:

a stage configured to support the structure during measurements;

a measuring unit comprising:

an illumination system configured to direct incident light of substantially broad wavelengths band with a predetermined solid angle of light propagation, toward a surface of the structure during a measurement; and a detection system configured to detect light propagating from the surface of the structure during measurements, wherein the measuring unit is configured to generate one or more output signals in response to the detected light during measurements; and a computer system coupled to the measuring unit and configured and operable for receiving and analyzing said output signals to extract spectral information, and fitting said spectral information to reference data to determine said parameters of the patterned structure, wherein said reference data is indicative of weighted diffraction efficiency at plurality of angles of incidence around an average direction of said predetermined solid angle of light propagation toward a surface of the structure during measurement.

2. The system of claim 1, wherein the stage is further configured to move laterally during measurements.

3. The system of claim 1, wherein the stage is further configured to move rotatably during measurements.

4. The system of claim 1, wherein the stage is further configured to move laterally and rotatably during measurements.

5. The system of claim 1, wherein the illumination system comprises a single light source.

6. The system of claim 1, wherein the illumination system comprises more than one light source.

7. The system of claim 1, wherein the detection system comprises a single light detector.

8. The system of claim 1, wherein the detection system comprises more than one light detector.

9. The system of claim 1, wherein the measuring unit comprises a scatterometer.

10. The system of claim 1, wherein the measuring unit comprises a spectroscopic scatterometer.

11. The system of claim 1, wherein the measuring unit comprises a reflectometer.

12. The system of claim 1, wherein the measuring unit comprises a spectroscopic reflectometer.

13. The system of claim 1, wherein the measuring unit comprises a bright field imaging channel.

14. The system of claim 1, wherein the measuring unit comprises a dark field imaging channel.

15. The system of claim 1, wherein the measuring unit comprises bright field and dark field imaging channels.

16. The system of claim 1, wherein the measuring unit utilizes an ellipsometer light propagation scheme.

17. The system of claim 1, wherein the measuring unit utilizes a spectroscopic ellipsometer light propagation scheme.

18. The system of claim 1 wherein the measuring unit utilizes a two-beam spectrophotometer scheme.

19. The system of claim 1, wherein the measuring unit defines a first measurement channel and a second measurement channel, and wherein the first and second measurement channels are selected from of the following channels: a scatterometer, a spectroscopic scatterometer, a reflectometer, a spectroscopic reflectometer, a bright field imaging, a dark field imaging, bright field and dark field imaging, an ellipsometer, a spectroscopic ellipsometer, a two-beam spectrophotometer, multi-incidence angle reflectometer, multi-incidence angle ellipsometer.

20. The system of claim 1, wherein the measuring unit defines a first measurement channel and a second measurement channel, and wherein optical elements of the first measurement channel comprise optical elements of the second measurement channel.

21. The system of claim 20, wherein the optical elements include at least one polarizer.

22. The system of claim 21, wherein the polarizer is accommodated in optical paths of the incident light propagating towards the structure and the light propagating from the structure towards the detection system.

23. The system of claim 21, wherein the polarizer is mounted for rotation so as to change its preferred polarization.

24. The system of claim 21, wherein the polarizer is mounted so as to be shifted between its two operational positions to be in or out of an optical path of light propagating through the measuring unit.

25. The system of claim 1, wherein the processor is configured to determine, from the one or more output signals during measurements, the structure parameter selected from a surface profile of the structure, a surface relief of a layer on the structure, and a topography parameter of a feature of the structure.

26. The system of claim 25, wherein the system is coupled to a process tool selected from a tool of a lithography tools arrangement and an etching tool.

27. The system of claim 1, wherein the system is configured to determine at least the parameters of the structure substantially simultaneously during measurements.

28. The system of claim 1, wherein the illumination system is configured to direct the incident light to multiple measurement sites on the surface of the structure, and wherein the detection system is configured to detect light propagating from the multiple measurement sites on the surface of the structure such that one or more of the parameters of the structure can be determined at the multiple measurement sites.

29. The system of claim 1, wherein the system is coupled to a processing tool.

30. The system of claim 1, wherein the system is coupled to a processing tool, and wherein the system is at least partly disposed within the processing tool.

31. The system of claim 1, wherein the system is coupled to a processing tool, and wherein the system is integrated with a processing tool arrangement.

32. The system of claim 1, wherein the system is coupled to a processing tool, and wherein the processing tool comprises a robot means configured to move the structure to the stage for measurements.

33. The system of claim 1, wherein the system is coupled to a processing tool, and wherein the system is configured to determine the parameters of the structure while the structure is between processing steps.

34. The system of claim 1, wherein the support stage supports the structure during measurements in a horizontal plane.

35. The system of claim 1, wherein the system is coupled to a processing tool, and wherein the processing tool is selected from the group including a tool of a lithography tools arrangement and an etching tool.

36. The system of claim 1, wherein the stage and the measuring unit are configured as an integrated system being disposed within a processing tool.

37. The system of claim 1, wherein the support stage and the measuring unit are configured as an integrated system being coupled to a processing tool.

38. The system of claim 1, wherein the support stage and the measuring unit are disposed with respect to a processing tool such that a robot of the processing tool is capable of supplying the structure between the processing tool and the measuring unit.

39. The system of claim 1, wherein the processor is coupled to a processing tool and is configured to adjust a parameter of the processing tool in response to the determined parameters of the structure.

40. The system of claim 1, wherein the processor is configured to carry out statistical analysis of the determined parameters of the structure and parameters of a plurality of structures during measurements.

41. The system of claim 40, wherein the statistical analysis includes at least one of the following: in-wafer statistics, wafer-to-wafer statistics, lot-to-lot statistics, module-to-module statistics.

42. The system of claim 1, wherein the processor is configured to compare the determined parameter of the structure to a predetermined range for this parameter.

43. The system of claim 1, wherein the processor is configured to adjust a parameter of a processing tool coupled to the measuring unit in response to the determined parameters of the structure using a feedback control technique.

44. The system of claim 1, wherein the processor is configured to adjust a parameter of a processing tool coupled to the measuring unit in response to the determined parameters of the structure using a feedforward control technique.

45. The system of claim 1, wherein the processor is configured to create a database, wherein the database comprises the determined parameters of the structure.

46. The system of claim 45, wherein the processor is configured to calibrate the measuring unit using the database.

47. The system of claim 46, wherein the processor is configured to monitor output signals generated by the measuring unit using the database.

48. The system of claim 46, wherein the database comprises the parameters of a plurality of structures.

49. The system of claim 48, wherein the parameters of the plurality of structures are determined using the measuring unit.

50. The system of claim 48, wherein the parameters of the plurality of structures are determined using a plurality of measuring units.

51. The system of claim 50, wherein the processor is coupled to the plurality of measuring units.

52. The system of claim 51, wherein the processor is configured to calibrate the plurality of measuring units using the database.

53. The system of claim 51, wherein the processor is configured to monitor output signals generated by the plurality of measuring units using the database.

54. The system of claim 1, wherein the system is configured to determine the parameters of the structure at more than one site on the structure, wherein the structure comprises a wafer, and wherein the processor is configured to adjust at least one parameter of a wafer processing tool in response to at least one of the determined parameters of the structure at the more than one site on the structure to reduce within wafer variation of at least one of the determined parameters.

55. The system of claim 1, wherein the processor is coupled to a structure processing tool.

56. The system of claim 55, wherein the processor is configured to adjust a parameter of the processing tool in response to the determined parameters using a feedback control technique.

57. The system of claim 55, wherein the processor is configured to adjust a parameter of the processing tool in response to the determined parameters using a feedforward control technique.

58. The system of claim 55, wherein the processor is configured to monitor a parameter of the processing tool.

59. The system of claim 58, wherein the processor is configured to determine a relationship between the determined parameters and the monitored parameter of the processing tool.

60. The system of claim 59, wherein the processor is configured to adjust a parameter of the processing tool in response to the relationship.

61. The system of claim 1, wherein the processor is coupled to a plurality of measuring units, and wherein each of the plurality of measuring units is coupled to a processing tool.

62. The system of claim 1, wherein the processor comprises a local processor coupled to the measuring unit and a remote controller coupled to the local processor, wherein the local processor is configured to at least partially process the one or more output signals during measurements, and wherein the remote controller is configured to further process said partially processed output signals.

63. The system of claim 62, wherein the local processor is configured to determine the parameters of the structure.

64. The system of claim 62, wherein the remote controller is configured to determine the parameters of the structure.

65. The system of claim 1, wherein the measuring unit comprises a calibration channel configured for measuring a fraction of the illuminating light to determine its characteristic, simultaneously with said measurements.

66. The system of claim 65, wherein said calibration channel is configured to measure spectral characteristics of the illuminating light.

67. The system of claim 66, wherein said calibration channel comprises a spectrometer.

68. The system of claim 65, wherein said calibration channel is configured to measure intensity variations of the illuminating light.

69. The system of claim 68, wherein said calibration channel comprises a photodiode.

70. The system of claim 1, comprising more than one measuring unit, the measuring units for applying measurements to structures associated with different processing toots, the measuring units being coupled to a common control system via a communication network.

71. The system of claim 70, wherein said different processing tools are operable to perform the same manufacturing step.

72. The system of claim 70, wherein said different processing tools are operable to perform different manufacturing steps.

73. The system of claim 70, wherein said different processing tools are associated with same FAB.

74. The system of claim 70, wherein said different processing tools are associated with different FABs.

75. The system of claim 70, wherein said processor is a part of said common control system.

76. The system of claim 70, comprising more than one processor, each of the measuring units being coupled to a corresponding one of the processors, the processors being connected to the common control system via the communication network.

77. The system of claim 70, wherein the common control system is accommodated outside a production line.

78. The system of claim 70, wherein said common computer system is connectable to a host machine of a FAB via said communication network.

79. The system of claim 78, wherein said connection between the computer system and the host machine enables closed loop control of a corresponding processing tool.

80. The system of claim 70, wherein the common control system is responsible for information from a user to prepare certain database to be available by a corresponding measuring unit via the communication network.

81. The system of claim 1, wherein the layer characteristic includes a layer thickness.

82. The system of claim 1, comprising at least one sensor configured for sensing at least one internal parameter of the measuring unit, thereby enabling monitoring of the operation of the measuring unit.

83. The system of claim 82, wherein the sensed parameter includes at least one of temperature and light source condition.

84. The system of claim 82, wherein the sensor is configured to generate an alarm signal in case of malfunction or evidence for required preventive maintenance.

85. The system of claim 1, comprising an optical character recognition (OCR) channel.

86. The system of claim 85, wherein the OCR channel includes an optical detector and a controller running OCR software.

87. The system of claim 85, wherein the OCR channel includes at least one of optical elements of the measuring unit.

88. The system of claim 85, wherein the optical detector of the OCR channel is connectable to the processor.

89. The system of claim 85, wherein the optical detector of the OCR channel is connectable to a central controller.

90. A method for determining a critical dimension and a layer characteristic parameter of a structure, the method comprising:
   disposing the structure upon a stage;
   subjecting the structure on the stage to measurements by measuring unit comprising an illumination system and a detection system, the measurements comprising operating the illumination system for directing light toward a surface of the structure with a predetermined solid angle of light propagation, detecting by said detection system light propagating from the surface of the structure, and generating one or more output signals in response to the detected light; and
   processing data indicative of the one or more output signals, said processing comprising extracting spectral information from said data, and fitting said spectral information to certain reference data to determine said parameters of the patterned structure, the reference data being indicative weighted diffraction efficiency at plurality of angles of incidence around an average direction of said predetermined solid angle of light propagation toward a surface of the structure during measurement.

91. A computer-implemented method for controlling a system comprising a measuring unit and being configured to determine a critical dimension and a layer characteristic parameters of a structure, the method comprising:
   controlling operation of the measuring unit, wherein the measuring unit comprises an illumination system and a detection system, said controlling comprising:
   controlling the illumination system to direct light toward a surface of the structure with a predetermined solid angle of light propagation;
   controlling the detection system to detect light propagating from the surface of the structure and generate data indicative of one or more output signals responsive to the detected light; and
   processing said data indicative of the one or more output signals, said processing comprising extracting spectral information from said data, and fitting said spectral information to certain reference data to determine said parameters of the patterned structure, the reference data being indicative of weighted diffraction efficiency at plurality of angles of incidence around an average direction of said predetermined solid angle of light propagation toward a surface of the structure during measurement.

92. A method for fabricating a semiconductor device, the method comprising:
   forming a portion of the semiconductor device upon a structure;
   disposing the structure upon a stage, and subjecting the structure to measurements by a measuring unit comprising an illumination system and a detection system, the measurements comprising operating the illumination system for directing light toward a surface of the structure with a predetermined solid angle of light propagation, detecting by said detection system light propagating from the surface of the structure, and generating data indicative of one or more output signals in response to the detected light; and
   processing said data indicative of the one or more output signals to determine said parameters of the structure, said processing comprising extracting spectra information from said data, and fitting said spectral information to certain reference data to determine a critical dimension and a layer characteristic parameter of the structure, the reference data being indicative of weighted diffraction efficiency at plurality of angles of incidence around an average direction of said predetermined solid angle of light propagation toward a surface of the structure during measurement.

93. The method of claim 92, comprising identifying the structure under measurements by the structure identity number.

94. The method of claim 93, wherein said identifying comprises applying to the structure an optical character recognition (OCR).

95. A system configured to determine a critical dimension and a layer characteristic parameter of a structure, the system comprising:
   a stage configured to support the structure;
   a measuring unit comprising: an illumination system configured to direct light toward a surface of the structure during measurements with a predetermined solid angle of light propagation; and a detection system coupled to the illumination system and configured to detect light propagating from the surface of the structure during measurements, wherein the measuring unit is configured to generate one or more output signals responsive to the detected light;
   a computer system comprising a local processor coupled to the measuring unit and configured to at least partially process the one or more output signals, and a remote controller coupled to the local processor, wherein the remote controller is configured to receive the at least partially processed one or more output signals and determine said parameters of the structure from the at least partially processed one or more output signals, the local and remote processors operating together to carry out the following: extracting spectral information from said data, and fitting said spectral information to certain reference data to determined said parameters of the patterned structure, the reference data being indicative of weighted diffraction efficiency at plurality of angles of incidence around an average direction of said predetermined solid angle of light propagation toward a surface of the structure during measurement.

96. A method for determining a critical dimension and a layer characteristic parameters of a structure, the method comprising:

disposing the structure upon a stage, and subjecting the structure to measurements by a measuring device, comprises an illumination system and a detection system, measurements comprising operating the illumination system for directing light toward a surface of the structure with a predetermined solid angle of light propagation, detecting by said detection system light propagating from the surface of the structure, and generating one or more output signals responsive to the detected light; and processing the one or more output signals to determine said parameters of the structure, said processing comprising extracting spectral information from said data, and fitting said spectral information to certain reference data to determine said parameters of the patterned structure, the reference data being indicative of weighted diffraction efficiency at plurality of angles of incidence around an average direction of said predetermined solid angle of light propagation toward a surface of the structure during measurement, processing being carried out by:

at least partially processing the one or more output signals using a local processor coupled to the measuring unit;

sending data resulting from the partial processing from the local processor to a remote controller; and further processing said data resulting from the partial processing at the remote controller.

\* \* \* \* \*

UNITED STATES PATENT AND TRADEMARK OFFICE
CERTIFICATE OF CORRECTION

| | | |
|---|---|---|
| PATENT NO. | : 7,477,405 B2 | Page 1 of 1 |
| APPLICATION NO. | : 10/724113 | |
| DATED | : January 13, 2009 | |
| INVENTOR(S) | : Finarov et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1131 days.

Signed and Sealed this
Fourth Day of October, 2011

David J. Kappos
*Director of the United States Patent and Trademark Office*